United States Patent
Gao et al.

(10) Patent No.: US 10,513,922 B2
(45) Date of Patent: Dec. 24, 2019

(54) METHOD AND DEVICE FOR DOWNHOLE CORROSION AND EROSION MONITORING

(71) Applicant: Halliburton Energy Services, Inc., Houston, TX (US)

(72) Inventors: Li Gao, Katy, TX (US); Michael T. Pelletier, Houston, TX (US); Robert S. Atkinson, Richmond, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/431,011

(22) PCT Filed: Sep. 6, 2013

(86) PCT No.: PCT/US2013/058444
§ 371 (c)(1),
(2) Date: Mar. 25, 2015

(87) PCT Pub. No.: WO2015/034516
PCT Pub. Date: Mar. 12, 2015

(65) Prior Publication Data
US 2015/0240627 A1  Aug. 27, 2015

(51) Int. Cl.
*E21B 47/12* (2012.01)
*E21B 41/02* (2006.01)
(Continued)

(52) U.S. Cl.
CPC ............ *E21B 47/122* (2013.01); *E21B 41/02* (2013.01); *G01N 17/04* (2013.01); *G01V 3/26* (2013.01)

(58) Field of Classification Search
CPC ....... E21B 47/122; E21B 41/02; G01N 17/04; G01V 3/26
See application file for complete search history.

(56) References Cited

U.S. PATENT DOCUMENTS 3,609,549 A   9/1971 Hausler et al.
3,999,121 A  12/1976 Taylor, Jr.
(Continued)

FOREIGN PATENT DOCUMENTS

EP      2124035       11/2009
JP  2011137774 A       7/2011
(Continued)

OTHER PUBLICATIONS

Saeidi, Nooshin, et al. "Design and fabrication of corrosion and humidity sensors for performance evaluation of chip scale hermetic packages for biomedical implantable devices." Microelectronics and Packaging Conference, 2009. EMPC 2009. European. IEEE, 2009.*

(Continued)

*Primary Examiner* — Robert J Eom
(74) *Attorney, Agent, or Firm* — Baker Botts L.L.P.

(57) ABSTRACT

Methods and systems for monitoring material loss in a downhole environment arising from corrosion and/or erosion include placing a downhole sensor in a borehole. The resistance of the downhole sensor is measured using a four-probe resistance technique in which a power source is provided at two electrodes of the downhole sensor and voltage is measured at two voltage taps. A rise in voltage over time indicates loss of conductive material on the downhole sensor. The conductive material on the downhole sensor may be formed to provide discrete voltage increases for improving reliability of material loss and/or rate of material loss resistance measurements.

21 Claims, 5 Drawing Sheets

(51) Int. Cl.
*G01N 17/04* (2006.01)
*G01V 3/26* (2006.01)

(56) References Cited

U.S. PATENT DOCUMENTS

| | | | |
|---|---|---|---|
| 4,338,097 | A | 7/1982 | Turner et al. |
| 5,139,627 | A | 8/1992 | Eden et al. |
| 5,627,749 | A | 5/1997 | Waterman et al. |
| 5,888,374 | A | 3/1999 | Pope et al. |
| 6,132,593 | A | 10/2000 | Tan |
| 6,383,451 | B1 | 5/2002 | Young-Geun et al. |
| 6,564,620 | B1 | 5/2003 | Paul |
| 6,946,855 | B1 | 9/2005 | Hemblade |
| 7,034,553 | B2 | 4/2006 | Giboe |
| 7,388,386 | B2 | 6/2008 | Ramgopal et al. |
| 7,915,901 | B2 | 3/2011 | Bell et al. |
| 9,109,988 | B2 * | 8/2015 | Morgan ............ G01N 17/04 |
| 2004/0155670 | A1 | 8/2004 | Yang et al. |
| 2006/0162431 | A1 * | 7/2006 | Harris ............ G01N 17/006 73/86 |
| 2010/0025110 | A1 | 2/2010 | John et al. |
| 2011/0187395 | A1 * | 8/2011 | Morgan ............ G01N 17/04 324/700 |
| 2012/0007617 | A1 | 1/2012 | Fisseler et al. |
| 2012/0132526 | A1 | 5/2012 | Hammonds et al. |
| 2013/0056626 | A1 | 3/2013 | Shen et al. |

FOREIGN PATENT DOCUMENTS

| | | | |
|---|---|---|---|
| WO | WO 00/45148 | * | 8/2000 |
| WO | 2014-009696 | | 1/2014 |

OTHER PUBLICATIONS

Harris et al., "A corrosion prediction model and corrosion sensors for corrosion management" 1$^{st}$ World Congress on Corrosion in the Military, 1$^{st}$ Jun. 2005, 8 pages.*
International Search Report and Written Opinion, Application No. PCT/US2013/058444, 10 pages, dated Jun. 2, 2014.
van der Pauw, A Method of Measuring Specific Resistivity and Hall Effects of Discs with Arbitrary Shape. *Philips Research Reports*, vol. 13, pp. 1-9, Feb. 1958.
Fallon and A. Walton, Measurement of Minimum Line Widths Using Fallon Ladders, in *Proceedings of IEEE International Conference on Microelectronic Test Structures*, (Sitges, Spain), pp. 263.268, Mar. 1993.
Extended European Search Report, Application No. 13893150.6; 7 pages, dated Feb. 9, 2016.
Australian Office Action, Application No. 2013399633; 3 pages, dated Feb. 16, 2016.
International Preliminary Report on Patentability, Application No. PCT/US2013/058444; 6 pages, dated Mar. 8, 2016.
European Examination Report, Application No. 2013399633; 4 pages, dated Aug. 5, 2016.
Office Action for Saudi Arabian Patent Application No. GC 2014-27869, dated Feb. 15, 2018; 4 pages.

* cited by examiner

METHOD AND DEVICE FOR DOWNHOLE CORROSION AND EROSION MONITORING

RELATED APPLICATION

This application is a U.S. National Stage Application of International Application No. PCT/US2013/058444 Sep. 6, 2013, which designates the United States, and which is incorporated herein by reference in its entirety.

BACKGROUND

This disclosure relates generally to subterranean drilling operations and, more particularly, to monitoring corrosion and erosion in a downhole environment.

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a borehole at a desired well site, treating the borehole to optimize production of hydrocarbons, and performing the necessary steps to produce and process the hydrocarbons from the subterranean formation.

During drilling and production operations, various pieces of equipment are exposed to the downhole environment where corrosion and erosion, particularly of metal parts, may occur. Due to the presence of corrosive chemicals, such as, but not limited to, $H_2S$ and $CO_2$, and abrasive particulates, metallic equipment in the downhole environment of well installations is subject to corrosion and erosion. Such corrosion and erosion may represent a serious risk of equipment failure. Particularly when downhole equipment fails unexpectedly, for example, due to unknown degrees of corrosion and erosion, a number of associated economic disadvantages for a drilling operator may result, such as undesirable downtime of drilling operations and unplanned repairs and replacement of affected downhole equipment.

FIGURES

Some specific exemplary embodiments of the disclosure may be understood by referring, in part, to the following description and the accompanying drawings.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and are not exhaustive of the scope of the disclosure.

DESCRIPTION OF PARTICULAR EMBODIMENT(S)

The present disclosure relates generally to well drilling operations and, more particularly, to monitoring corrosion and erosion in a downhole environment.

Illustrative embodiments of the present disclosure are described in detail herein. In the interest of clarity, not all features of an actual implementation may be described in this specification. It will of course be appreciated that in the development of any such actual embodiment, numerous implementation specific decisions must be made to achieve the specific implementation goals, which will vary from one implementation to another. Moreover, it will be appreciated that such a development effort might be complex and time consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the well below), or otherwise nonlinear boreholes in any type of subterranean formation. Embodiments may be applicable to injection wells as well as production wells, including natural resource production wells such as hydrogen sulfide, hydrocarbons or geothermal wells. Devices and methods in accordance with embodiments described herein may be used in one or more of wireline, slickline, measurement while drilling (MWD) and logging while drilling (LWD) operations. Embodiments described below with respect to one implementation, such as wireline, are not intended to be limiting. Embodiments may be implemented in various formation tools suitable for measuring, data acquisition and/or recording data along sections of the formation that, for example, may be conveyed through flow passage in tubular string or using a wireline, slickline, tractor, piston, piston-tractor, coiled tubing, downhole robot or the like.

Figure 1:
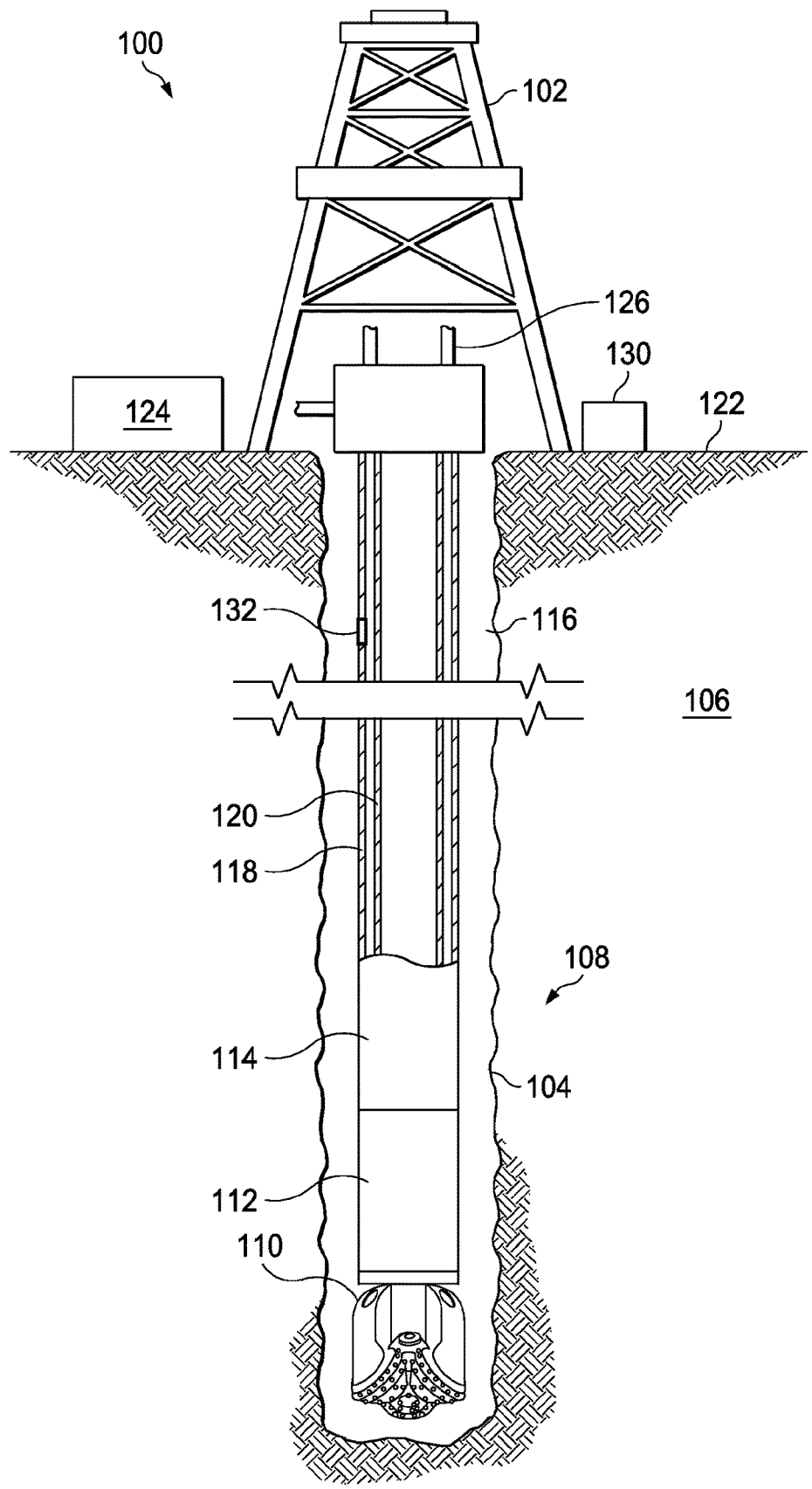
FIG. 1 is a block diagram of selected elements of an embodiment of an example drilling system.

FIG. 1 shows an existing drilling system 100. The drilling system 100 includes a rig 102 mounted at the surface 122, positioned above a borehole 104 within a subterranean formation 106. The rig 102 may be connected to multiple drilling pipes 118 and 120 via a top drive 126. The drilling system 100 may include a pipe-in-pipe drilling system where an inner pipe 120 is disposed within an outer pipe 118. Drilling muds, for example, may be pumped into the borehole 104 within the annulus defined by inner pipe 120 within outer pipe 118. The drilling mud may be pumped downhole through bottom hole assembly (BHA) 108 to drill bit 110. The BHA 108 may include a corrosion/erosion monitoring tool 114 and/or other LWD/MWD element 112, which may be coupled to outer pipe 118 and inner pipe 120. In certain embodiments, the drilling fluid may return to the surface 122 within annulus 116, or be diverted into inner pipe 120. A control unit 124 at the surface 122 may control the operation of at least some of the drilling equipment.

In FIG. 1, drilling system 100 may further include material loss monitor 130, which may be coupled to downhole sensor 132 via a wireline (not shown) in an exemplary communication embodiment. In other embodiments (not shown), downhole sensor 132 may communicate with material loss monitor 130 via various means, that may depend upon a placement of downhole sensor 132. In some embodiments, at least a portion of downhole sensor 132 and/or related equipment may be located within the pipe-in-pipe drilling system. Although material loss monitor 130 is depicted in drilling system 100 as being located at surface 122, material loss monitor 130 may be positioned as desired for a particular operation, including, at least in part, within borehole 104. Material loss monitor 130 may include a computer system (see FIG. 7) and associated instrumentation (see also FIGS. 4 and 5) for performing downhole material loss monitoring for corrosion and/or erosion processes, as described herein.

In operation, as drilling mud circulates past various downhole components of drilling system 100, corrosion and/or erosion of the downhole components may occur during normal operation. The corrosion and/or erosion may adversely affect performance and service lifetimes of the downhole components. Corrosion refers to undesirable chemical reactions that may consume a material from which a pipe-in-pipe drilling system, and/or other equipment (not shown) is formed. Erosion refers to mechanical abrasion, for example, from exposure to abrasive particles in a pressurized drilling fluid, which may cause material to be eroded and physically removed over time. Thus, corrosion and erosion may represent separate material loss processes that undesirably consume material from which downhole equipment is formed. Even though a corrosion process and an erosion process may occur concurrently, each process may be selective for a material composition of the affected equipment. For example, a rate of the corrosion process may depend upon a specific composition of steel used for forming downhole components of the pipe-in-pipe drilling system. Also, a rate of the erosion process may depend upon a hardness (or toughness) of a downhole material, which may also depend upon composition. The erosion process may further depend upon a hardness of particulate matter found in the drilling fluid that acts as an abrasive and may accordingly depend upon a geological composition of subterranean formation 106. Also, although downhole sensor 132 is shown mounted on outer pipe 118, it is note that in other embodiments, downhole sensor may be mounted in different arrangements, for example, on a surface of corrosion/erosion monitoring tool 114.

As will be described in further detail herein, corrosion/erosion monitoring tool 114 may be equipped for monitoring corrosion and/or erosion using downhole sensor 132 in a manner that mimics corrosion and/or erosion of at least one downhole component, in order to ascertain a rate of corrosion and/or erosion of the downhole components. Corrosion/erosion monitoring tool 114 may also determine whether the corrosion/erosion processes have damaged a given downhole component to an unacceptable level by removing so much material as to warrant replacement of the downhole component. Furthermore, material loss monitor 130, in conjunction with downhole sensor 132, may enable monitoring of material loss in the downhole environment from corrosion and/or erosion in a manner that is relatively insensitive to noise and that may be chemically specific for particular material compositions and/or reactants.

Figure 2A:
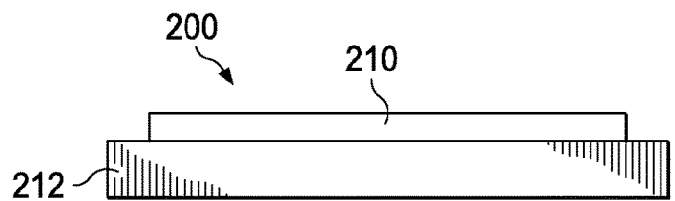
FIG. 2A is a block diagram of selected elements of an embodiment of a downhole sensor.

Referring now to FIG. 2A, a block diagram of selected elements of an embodiment of downhole sensor 200 is illustrated. As shown in the sectional depiction of FIG. 2A, downhole sensor 200 may include conductive portion 210 and insulating substrate 212. In various embodiments, conductive portion 210 may be a thick or thin conductive layer, such as a metal film. Conductive portion 210 may be deposited, or grown, on insulating substrate 212 using a variety of techniques, such as sputtering, thermal evaporation, laser ablation, atomic layer deposition, chemical vapor deposition, etc. In some embodiments, conductive portion 210 may be a metal sheet or foil that is joined with insulating substrate 212 using an adhesive (not shown). In particular embodiments, a chemical composition of conductive portion 210 may be selected to match a chemical composition of a downhole component in the borehole, which conductive portion 210 is designed to mimic in terms of material loss due to corrosion and/or erosion. A material composition of insulating substrate 212 may be selected for electrical insulation, chemical inertness in the downhole environment, as well as toughness/hardness in order to be resistant to material loss from corrosion and/or erosion. In one example, insulating substrate 212 includes an alumna ceramic.

Figure 2B:
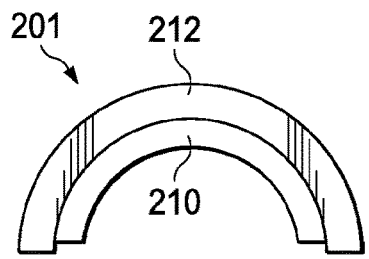
FIG. 2B is a block diagram of selected elements of an embodiment of a downhole sensor.

Referring now to FIG. 2B, a block diagram of selected elements of an embodiment of downhole sensor 201 is illustrated. As shown in the sectional depiction of FIG. 2B, downhole sensor 201 may include conductive portion 210 and insulating substrate 212, as described previously with respect to FIG. 2A. As shown, downhole sensor 201 has been formed with a curved geometry to conform to a tubular structure, such as a borehole casing and/or a drill string, among other examples of downhole equipment and components. Furthermore, in some embodiments, insulating substrate 212 may be formed to be mechanically flexible, for example, to be able to conform to an arbitrary geometry (not shown) in the downhole environment. The mechanical flexibility may arise, at least in part, from a geometry and/or dimension of a particular instance of insulating substrate 212. The mechanical flexibility may also arise, at least in part, from a material composition of insulating substrate 212.

Figure 2C:
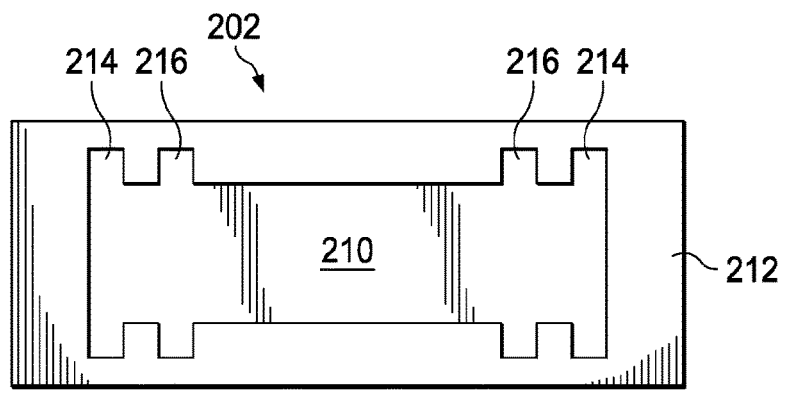
FIG. 2C is a block diagram of selected elements of an embodiment of a downhole sensor.

Referring now to FIG. 2C, a block diagram of selected elements of an embodiment of downhole sensor 202 is illustrated. As shown in FIG. 2C, downhole sensor 202 may include conductive portion 210 and insulating substrate 212, as described previously with respect to FIG. 2A. In FIG. 2C, downhole sensor 202 is shown in a top view, yet may have a similar sectional portrait as downhole sensor 200 (see FIG. 2A) or downhole sensor 201 (see FIG. 2B). As shown in FIG. 2C, conductive portion 210 is formed in a distinct pattern to facilitate resistance measurements in a four-probe configuration, in which two electrodes, represented by current taps 214, are used to inject electrical current from a current source (see FIG. 4) and two voltage taps 216 are used to measure a resulting voltage difference. The resistance R at any given time of downhole sensor 202 is given by Equation 1 below.

$$R = \frac{V}{I} = \frac{\rho}{t}\frac{L}{W} = R_s * g \qquad \text{Equation (1)}$$

In Equation 1, V is the voltage measured across voltage taps 216, I is the current across current taps 214, ρ is the resistivity of a material used to form conductive portion 210, g is a geometric factor equal to length L divided by width W of conductive portion 210, t is a thickness of conductive portion 210, and $R_s$ is a sheet resistance given by ρ/t. Thus, based on Equation 1, the thickness t of conductive portion 210 may be determined at any time from a resistance measurement. When the resistance measurements are repeated over time, the change in t over time may be determined and may be correlated with a rate of material loss due to corrosion and/or erosion in the downhole environment.

Figure 2D:
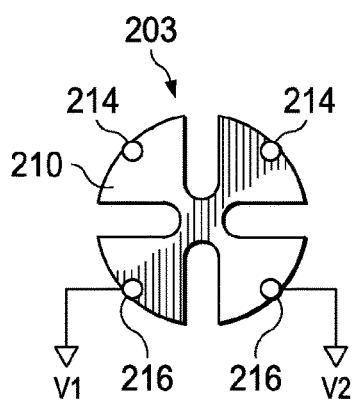
FIG. 2D is a block diagram of selected elements of an embodiment of a downhole sensor.

Referring now to FIG. 2D, a block diagram of selected elements of an embodiment of downhole sensor 203 is illustrated. As shown in FIG. 2D, downhole sensor 203 may include conductive portion 210 and insulating substrate 212 (not shown in FIG. 2D), as described previously with respect to FIG. 2A, although only conductive portion 210 is shown in FIG. 2D for descriptive clarity. In FIG. 2D, downhole sensor 203 is shown in a top view, yet may have a similar sectional portrait as downhole sensor 200 (see FIG. 2A) or downhole sensor 201 (see FIG. 2B). As shown in FIG. 2D, conductive portion 210 is formed in a distinct pattern to facilitate resistance measurements in a four-probe configuration, in which two current taps 214 are used to inject electrical current from a current source (see FIG. 4) and two voltage taps 216 are used to measure a resulting voltage difference. The design of downhole sensor 203 may be based on a Van der Pauw configuration, in which a symmetric structure is used to measure sheet resistance using a difference between voltages V1 and V2, as given by Equation 2.

$$R = \frac{V1 - V2}{I} \quad \text{Equation (2)}$$

Then, the sheet resistance $R_s$ and thickness t for downhole sensor 203 may be given by Equations 3 and 4.

$$R_s = \frac{\rho}{t} = \frac{\pi}{\ln(2)} R \quad \text{Equation (3)}$$

$$t = \frac{\ln(2)\rho}{\pi R} \quad \text{Equation (4)}$$

Figure 3A:
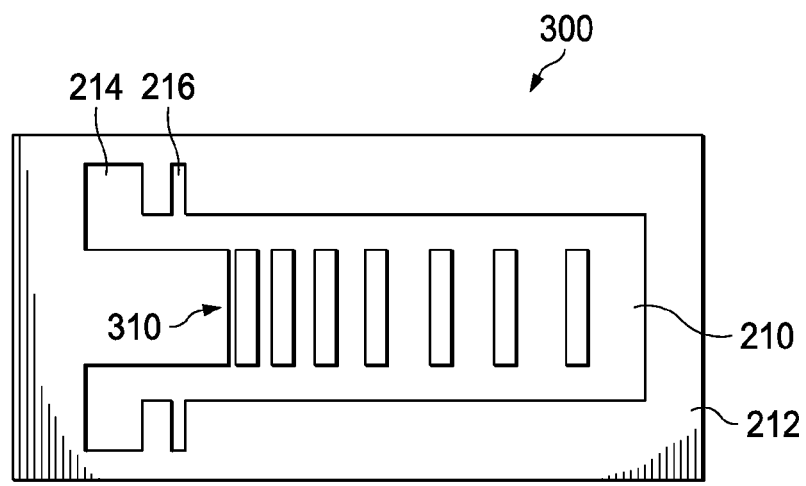
FIG. 3A is a block diagram of selected elements of an embodiment of a downhole sensor.

Turning now to FIG. 3A, a block diagram of selected elements of an embodiment of downhole sensor 300 is illustrated. As shown in FIG. 3A, downhole sensor 300 may include conductive portion 210 and insulating substrate 212, as described previously with respect to FIG. 2A. In FIG. 3A, downhole sensor 300 is shown in a top view, yet may have a similar sectional portrait as downhole sensor 200 (see FIG. 2A) or downhole sensor 201 (see FIG. 2B).

In FIG. 3A, downhole sensor 300 has been formed based on a Fallon ladder, in which electrical pathways 310 represent rungs on a ladder structure. Electrical pathways 310 in downhole sensor 300 may have individually varying widths and/or lengths, and accordingly, varying resistances. In particular embodiments, each electrical pathway 310 is associated with a unique cross-sectional area and, therefore, a unique contribution to an overall resistance of downhole sensor 300. As compared with downhole sensors 200, 201, 202, 203 (see FIGS. 2A-D), downhole sensor 300 may provide certain advantages for material loss determination. Specifically, due to an expected level of noise associated with small voltage signals arising from a low resistance of a metal structure, a differential increment of the voltage signal in a four-probe resistance configuration may be difficult to ascertain. Particularly when material loss rates are desired at relatively short time intervals, downhole sensor 300 may provide certain unique advantages by flowing current through electrical pathways 310. For example, when a particular one of electrical pathway 310 is ultimately severed due to material loss from corrosion and/or erosion, an overall change (i.e., reduction) in resistance of downhole sensor 300 may be a discrete value that results in a corresponding discrete change (i.e., increase) in the measured voltage. Since the discrete change in the measured voltage due to severing of electrical pathway 310 is generally greater than a change in voltage from a gradual loss of material in the downhole environment, downhole sensor 300 may provide indications of material loss with a higher degree of certainty than other types of conductivity probes.

In FIG. 3A, the dimensions and arrangement of electrical pathways 310 in downhole sensor 300 may be selected based on various factors. For example, a difference in cross-sectional area between any two adjacent electrical pathways 310 may be dimensioned such that a resulting voltage increase upon severing is statistically significant with respect to noise on the voltage signal. In certain embodiments, the resulting voltage change from severance of electrical pathway 310 may be at least a magnitude of a detection limit for a baseline voltage noise level, such as a noise level in the downhole environment. The detection limit may correspond to three (3) times a peak-peak value of the baseline voltage noise level. It is further noted that, as a result of improved sensitivity for certain measurement points due to the arrangement of electrical pathways 310, downhole sensor 300 may accordingly provide improved rate of material loss measurements with a higher degree of certainty than other arrangements of conductive portion 210. A rate of the material loss process may be determined, for example, by recording times at which at least two electrical pathways 310 are severed. In certain embodiments, downhole sensor 300 may be formed specifically to provide a desired number of distinct voltage signals resulting from severing of electrical pathways 310 in order to determine the rate of material loss. In given embodiments, an electrical pathway 310 included in downhole sensor 300 may be dimensioned to provide a characteristic value related to a particular downhole component, for example, by mimicking a failure to due material loss of the downhole component. In this manner, downhole sensor 300 may be used to provide a reliable pass/fail test at an arbitrary and/or desired time for a given downhole component. Although downhole sensor 300 provides greater sensitivity in certain aspects, as described above, downhole sensor 300 may still be used in a four-probe resistance configuration with a single current source and a single voltage measurement, which is advantageous in terms of cost and complexity.

Figure 3B:
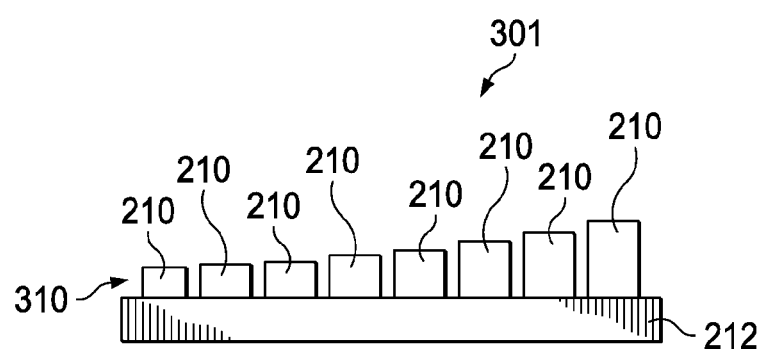
FIG. 3B is a block diagram of selected elements of an embodiment of a downhole sensor.

Advancing now to FIG. 3B, a block diagram of selected elements of an embodiment of downhole sensor 301 is illustrated. As shown in FIG. 3B, downhole sensor 301 may include conductive portion 210 and insulating substrate 212, as described previously with respect to FIG. 3A. In FIG. 3B, downhole sensor 301 is shown as a sectional view of an embodiment of downhole sensor 300, in which a thickness of each of electrical pathways 310 has been varied to vary the cross-sectional area.

As shown in FIGS. 3A and 3B, it will be understood that a combination of variation of width and/or thickness of electrical pathways 310 may be practiced in other embodiments. It is further noted that a material composition of at least one electrical pathway 310 may be varied (not shown) to achieve a desired chemical specificity with regard to corrosion reactions in the downhole environment. In this manner, downhole sensor 301 and/or 300 may be used to detect or identify the presence of a particular chemical species from a measured change in resistivity. For example, in the presence of aqueous hydrogen sulfide ($H_2S$), it is known that iron (Fe) may be oxidized to iron sulfide (FeS), which may be distinctly detected by resistance measurements using downhole sensor 301 and/or 300. Other dimensional and/or compositional variations for selective detection of material loss in the downhole environment may be practiced in different embodiments.

Figure 4:
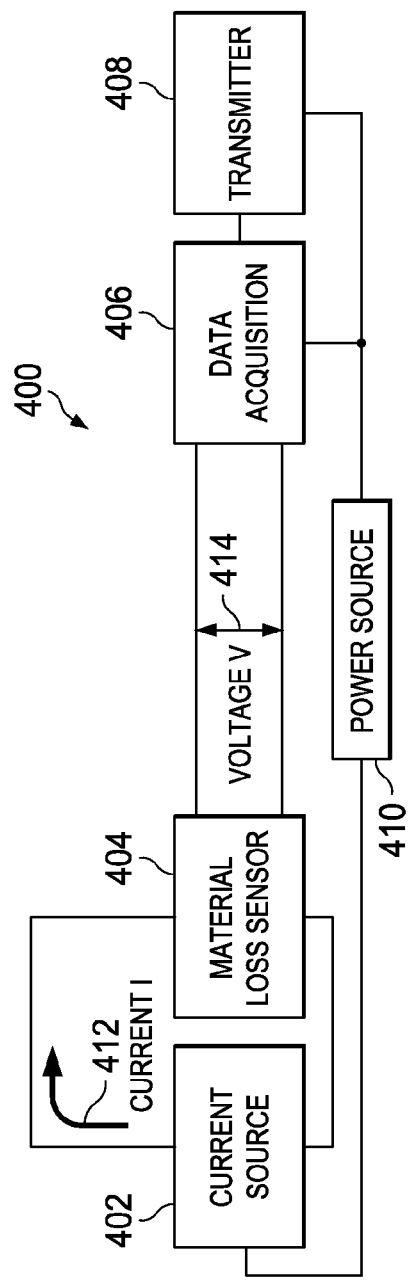
FIG. 4 is a block diagram of selected elements of an embodiment of a material loss monitor.

Referring now to FIG. 4, a block diagram of selected elements of an embodiment of material loss monitor 400 is illustrated. As shown, material loss monitor 400 may represent functionality for performing material loss resistance measurements, as described herein. In some embodiments, at least certain portions of shown in FIG. 4 may be implemented in material loss monitor 130 and/or downhole sensor 132 (see FIG. 2).

In FIG. 4, power source 410 may represent a source of electrical power used to power various elements. For example, power source 410 may provide electrical power to current source 402 for applying current 412 to material loss sensor 404 to perform resistance measurements. Power source 410 may also provide power for data acquisition 406, which measures voltage 414 across material loss sensor 404 as a result of current 412 being applied. Power source 410 may also provide power to transmitter 408, which may transmit measurement results to a computer system for further processing. Current source 402 may be a source of electrical current and may be coupled to material loss sensor 404 via two current taps (see FIGS. 3A, 3B). In certain embodiments, current source 402 may include a voltage source and a load resister (not shown) over which current is provided. Material loss sensor 404 may represent at least a portion of downhole sensors 200, 201, 202, 203, 300, 301 (see FIGS. 2A-2D, 3A, 3B). Data acquisition 406 may include a digitizer, such as an analog-digital converter, for acquiring and digitizing voltage values and/or calculating a thickness from measured voltage values. Transmitter 408 may be a wireline and/or wireless transmitter, in different embodiments.

In certain embodiments where line power is available, power source 410 may represent line power, while transmitter 408 may represent a wired communication channel that can provide galvanic and/or optical connectivity up the borehole. When line power is not available, power source 410 may represent a battery, while transmitter 408 may represent a wireless communication channel, such as an acoustic channel, mud pulse telemetry, electromagnetic telemetry, etc. It is noted that material loss monitor 400 may operate in a continuous and/or intermittent manner for performing material loss resistance measurements, as described herein.

Figure 5:
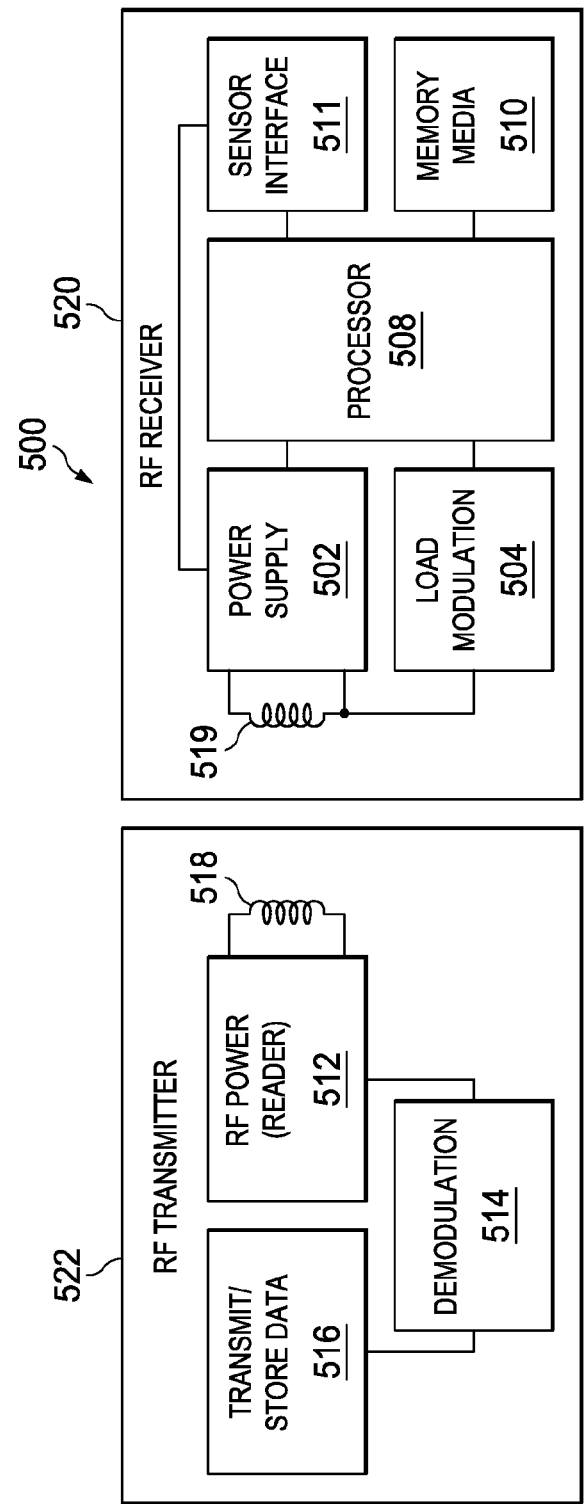
FIG. 5 is a block diagram of selected elements of an embodiment of a material loss monitor.

Referring now to FIG. 5, a block diagram of selected elements of an embodiment of material loss monitor 500 is illustrated. As shown, material loss monitor 500 may represent functionality for performing material loss resistance measurements, as described herein. As shown, material loss monitor 500 may represent an embodiment of passively powered material loss resistance measurements, such as in a permanent downhole installation where power and/or communication channels are not available.

In FIG. 5, material loss monitor 500 is shown comprising radio frequency (RF) transmitter 522 and RF receiver 520. RF transmitter 522 includes transmit/store data 516, demodulation 514, RF power (reader) 512, and antenna 518. RF receiver includes power supply 502, load modulation 504, processor 508, memory media 510, and sensor interface 511, which may include at least certain portions of material loss monitor 400 (see FIG. 4). RF receiver 520 may be permanently installed downhole, while RF transmitter 522 may be mounted on a logging tool that passes by RF receiver 520.

In operation, RF power (reader) 512 may radiate RF power from antenna 518 to antenna 519, which receives the RF power. Under control of processor 508 having access to memory media 510, at power supply 502, the RF power is rectified and a charge pump is used to provide DC power for other elements included in RF receiver 520, as well as for providing power for generating current at sensor interface 511. Sensor interface 511, which may include a downhole sensor and data acquisition, as described herein, may provide digitized voltage data. Processor 508 may then send current and voltage data via antenna 519 to antenna 518 using load modulation 504 to digitally switch a load impedance on and off, for example. The change in impedance is detected by demodulation 514 at RF transmitter 514 and demodulated into digital data. Transmit/store data 516 may, when available, transmit the digital data to a computer system, or when no external communication is available, may store the digital data for later retrieval, for example, when RF transmitter 522 surfaces from the borehole.

Figure 6:
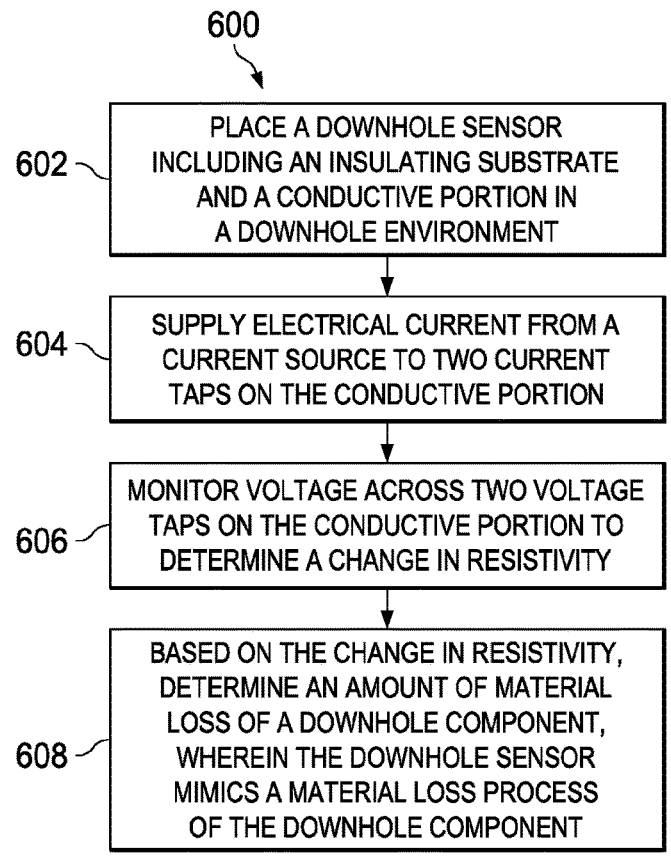
FIG. 6 depicts a flow chart of selected elements of an embodiment of a method for performing material loss resistance measurements.

Referring now to FIG. 6, a block diagram of selected elements of an embodiment of method 600 for performing material loss resistance measurements, as described herein, is depicted in flowchart form. It is noted that certain operations described in method 600 may be optional or may be rearranged in different embodiments.

In method 600, a downhole sensor including an insulating substrate and a conductive portion may be placed (operation 602) in a downhole environment. Electrical current from a current source may be supplied (operation 604) to two current taps on the conductive portion. Voltage across two voltage taps on the conductive portion may be monitored (operation 606) to determine a change in resistivity. Based on the change in resistivity, an amount of material loss of a downhole component may be determined (operation 608), wherein the downhole sensor mimics a material loss process of the downhole component.

Figure 7:
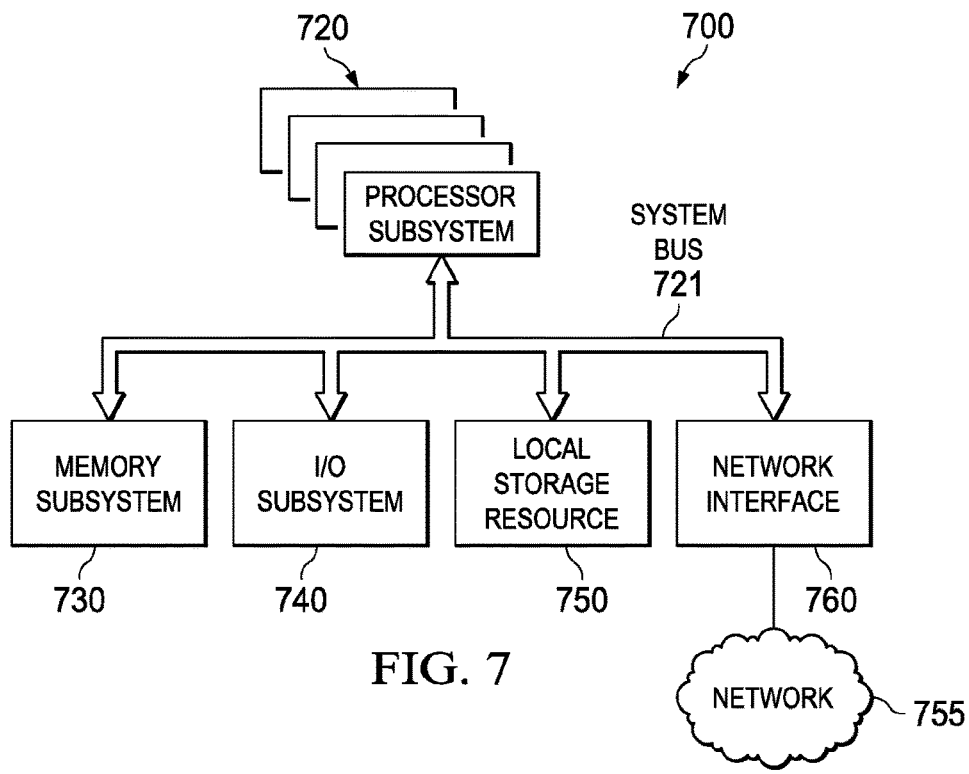
FIG. 7 is a block diagram of selected elements of an embodiment of a computer system.

Turning now to FIG. 7, a block diagram depicting selected elements of an embodiment of computer system 700 is illustrated. Computer system may be a personal computer (e.g., desktop or laptop), tablet computer, mobile device (e.g., personal digital assistant (PDA) or smart phone), server (e.g., blade server or rack server), a network storage device, or any other suitable device and may vary in size, shape, performance, functionality, and price. As shown in FIG. 7, components of computer system 700 may include, but are not limited to, processor subsystem 720, which may include one or more processors, and system bus 721 that communicatively couples various system components to processor subsystem 720 including, for example, a memory subsystem 730, an I/O subsystem 740, local storage resource 750, and a network interface 760. System bus 721 may represent a variety of suitable types of bus structures, e.g., a memory bus, a peripheral bus, or a local bus using various bus architectures in selected embodiments.

In FIG. 7, network interface 760 may be a suitable system, apparatus, or device operable to serve as an interface between computer system 700 and network 755. Network interface 760 may enable computer system 700 to communicate over network 755 using a suitable transmission protocol and/or standard, including, but not limited to, transmission protocols and/or standards enumerated below with respect to the discussion of network 755. In some embodiments, network interface 760 may be communicatively coupled via network 755 to a network storage resource (not shown). Network 755 may be implemented as, or may be a part of, a storage area network (SAN), personal area network (PAN), local area network (LAN), a metropolitan area network (MAN), a wide area network (WAN), a wireless local area network (WLAN), a virtual private network (VPN), an intranet, the Internet or another appropriate architecture or system that facilitates the communication of signals, data and/or messages (generally referred to as data). Network 755 may transmit data using a desired storage and/or communication protocol. Network 755 and its various components may be implemented using hardware, software, or any combination thereof.

As depicted in FIG. 7, processor subsystem 720 may include a system, device, or apparatus operable to interpret and/or execute program instructions and/or process data, and may include a microprocessor, microcontroller, digital signal processor (DSP), application specific integrated circuit (ASIC), or another digital or analog circuitry configured to interpret and/or execute program instructions and/or process data.

Also in FIG. 7, memory subsystem 730 may include a system, device, or apparatus operable to retain and/or retrieve program instructions and/or data for a period of time (e.g., computer-readable media). The computer system may include computer-readable instructions (not shown), for example stored by memory subsystem 730, to perform at least certain portions of the methods and data processing operations disclosed herein. Memory subsystem 730 may include random access memory (RAM), electrically erasable programmable read-only memory (EEPROM), read-only memory (ROM), a PCMCIA card, a solid state drive (SSD), flash memory, magnetic storage, opto-magnetic storage, and/or a suitable selection and/or array of volatile or non-volatile memory. Local storage resource 750 may include computer-readable media (e.g., hard disk drive, floppy disk drive, CD-ROM, and/or other type of rotating storage media, flash memory, EEPROM, and/or another type of solid state storage media) and may be generally operable to store instructions and/or data. Likewise, a network storage resource (not shown), for example, coupled to network 755, may include computer-readable media (e.g., hard disk drive, floppy disk drive, CD-ROM, and/or other type of rotating storage media, flash memory, EEPROM, magnetic storage devices, optical storage devices, network storage devices, cloud storage devices, or another suitable information storage device, and/or a combination of these devices and/or other type of solid state storage media) and may be generally operable to store instructions and/or data.

In FIG. 7, I/O subsystem 740 may include a system, device, or apparatus generally operable to receive and/or transmit data to/from/within system 700. In computer system 700, I/O subsystem 740 may represent, for example, a variety of communication interfaces, graphics interfaces, video interfaces, user input interfaces, and/or peripheral interfaces. Specifically, I/O subsystem 740 may include or support interfaces and/or instrumentation for downhole data acquisition and monitoring of corrosion and erosion, as described in detail herein.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. For example, the devices and methods described herein may be adapted for use to monitor oil piplelines, rather than in a downhole environment.

What is claimed is:

1. A downhole sensor for downhole monitoring of material loss in a downhole component in a borehole, the downhole component comprising:
    a conductive portion formed as a unitary solid structure having a chemical composition that matches a chemical composition of the downhole component in the borehole and comprising at least two electrodes and at least two electrical pathways, wherein each of the at least two electrical pathways in the conductive portion is formed with a cross-sectional area that is unique with respect to the other electrical pathway of the at least two electrical pathways in the conductive portion due to a variation in the thickness of each electrical pathway;
    a power source connected to the at least two electrodes to apply electrical current across the at least two electrical pathways;
    an insulating substrate upon which the conductive portion is placed; and
    a data acquisition unit connected to the at least two electrodes including circuitry to:
        measure a voltage across each of the at least two electrodes;
        calculate a thickness of the conductive portion based on the measured voltages; and
        determine, based upon a correspondence between a material composition of at least one of the at least two electrical pathways and a material loss process of a downhole component, an amount of erosion incurred by the downhole component by the erosion process,
        wherein the material loss process includes the erosion process.

2. The downhole sensor of claim 1, wherein a chemical composition of the conductive portion matches a chemical composition of the downhole component.

3. The downhole sensor of claim 1, wherein the conductive portion mimics the material loss process of the downhole component, and the material loss process further includes a corrosion process.

4. The downhole sensor of claim 3, wherein the material composition of the at least two electrical pathways corresponds to a reactivity with a chemical species found in a downhole fluid.

5. The downhole sensor of claim 3, wherein the material composition of the at least two electrical pathways corresponds to a hardness of a particulate found in a downhole fluid.

6. The downhole sensor of claim 3, wherein, an increase in a voltage occurs when the material loss process severs a first cross-sectional area for a first electrical pathway, and wherein the increase in the voltage corresponds to at least a detection limit for downhole monitoring of the voltage.

7. The downhole sensor of claim 6, wherein the detection limit is at least three times greater than a peak-to-peak noise level of the voltage.

8. The downhole sensor of claim 6, wherein the increase in the voltage is a characteristic value for a failure of the downhole component.

9. The downhole sensor of claim 1, wherein the insulating substrate and the conductive portion are formed with a curved geometry to conform to a tubular structure of at least a portion of a downhole component, and wherein the downhole component is selected from at least one of: a borehole casing and a drillstring.

10. The downhole sensor of claim 1, wherein the insulating substrate is mechanically flexible.

11. A downhole sensor for downhole monitoring of material loss in a downhole component in a borehole, the downhole component comprising:
a conductive portion formed as a unitary solid structure having a chemical composition that matches a chemical composition of the downhole component in the borehole and comprising at least two electrodes and at least two electrical pathways wherein each of the at least two electrical pathways in the conductive portion is formed with a cross-sectional area that is unique with respect to the other electrical pathway of the at least two electrical pathways in the conductive portion due to a variation in the thickness of each electrical pathway;
a power source connected to the at least two electrodes to apply electrical current across the at least two electrical pathways;
an insulating substrate upon which the conductive portion is placed; and
a data acquisition unit connected to the at least two electrodes including circuitry to:
measure a voltage across each of the at least two electrodes;
identify, based upon an increase in a voltage that a first cross-sectional area for a first electrical pathway of the at least two electrical pathways has been severed;
provide, based upon a correspondence between a material composition of at least one of the at least two electrical pathways and a material loss process of a downhole component, an indication that a detection limit has been reached.

12. The downhole sensor of claim 11, wherein a chemical composition of the conductive portion matches a chemical composition of the downhole component.

13. The downhole sensor of claim 11, wherein the conductive portion mimics the material loss process of the downhole component, and the material loss process includes a process selected from at least one of: a corrosion process and an erosion process.

14. The downhole sensor of claim 13, wherein the material loss process includes a corrosion process and the material composition of the at least two electrical pathways corresponds to a reactivity with a chemical species found in a downhole fluid.

15. The downhole sensor of claim 13, wherein the material loss process includes an erosion process and the material composition of the at least two electrical pathways corresponds to a hardness of a particulate found in a downhole fluid.

16. The downhole sensor of claim 11, wherein the detection limit is at least three times greater than a peak-to-peak noise level of the voltage.

17. The downhole sensor of claim 16, wherein the increase in the voltage is a characteristic value for a failure of the downhole component.

18. The downhole sensor of claim 11, wherein the insulating substrate and the conductive portion are formed with a curved geometry to conform to a tubular structure of at least a portion of a downhole component, and wherein the downhole component is selected from at least one of: a borehole casing and a drillstring.

19. The downhole sensor of claim 11, wherein the insulating substrate is mechanically flexible.

20. A downhole sensor for downhole monitoring of material loss, in a downhole component in a borehole, the downhole component:
a conductive portion formed as a unitary solid structure having a chemical composition that matches a chemical composition of the downhole component in the borehole and comprising at least two electrodes and at least two electrical pathways, wherein each of the at least two electrical pathways in the conductive portion is formed with a cross-sectional area that is unique with respect to the other electrical pathway of the at least two electrical pathways in the conductive portion due to a variation in the thickness of each electrical pathway;
a power source connected to the at least two electrodes to apply electrical current across the at least two electrical pathways; and
an insulating substrate upon which the conductive portion is placed; and
a data acquisition unit connected to the at least two electrodes including circuitry to:
measure a voltage across each of the at least two electrodes;
calculate a thickness of the conductive portion based on the measured voltages; and
determine, based upon a correspondence between a material composition of at least one of the at least two electrical pathways and a material loss process of a downhole component, an amount of corrosion incurred by the downhole component,
wherein the material loss process includes a corrosion process, and wherein the material composition is chemically specific to the corrosion process.

21. The downhole sensor of claim 20, wherein:
the corrosion process is an oxidization of iron (Fe) to iron sulfide (FeS) in the presence of aqueous hydrogen sulfide ($H_2S$); and
the material composition is iron (Fe).

* * * * *